(12) United States Patent
Jaeger et al.

(10) Patent No.: US 12,013,523 B2
(45) Date of Patent: Jun. 18, 2024

(54) IMMERSION OILS HAVING LONG SERVICE LIFE

(71) Applicant: Carl Zeiss Jena GmbH, Jena (DE)

(72) Inventors: Jakob Benedikt Jaeger, Heidenheim (DE); Matthias Krieg, Heidenheim (DE); Hans-Joachim Weippert, Aalen (DE)

(73) Assignee: Carl Zeiss Jena GmbH, Jena (DE)

( * ) Notice: Subject to any disclaimer, the term of this patent is extended or adjusted under 35 U.S.C. 154(b) by 256 days.

(21) Appl. No.: 17/213,549

(22) Filed: Mar. 26, 2021

(65) Prior Publication Data
US 2021/0302712 A1 Sep. 30, 2021

(30) Foreign Application Priority Data

Mar. 30, 2020 (DE) ...................... 10 2020 108 726.8

(51) Int. Cl.
*G02B 21/33* (2006.01)
*C07C 67/08* (2006.01)
*C07C 67/54* (2006.01)

(52) U.S. Cl.
CPC .............. *G02B 21/33* (2013.01); *C07C 67/08* (2013.01); *C07C 67/54* (2013.01); *C07C 2603/10* (2017.05)

(58) Field of Classification Search
None
See application file for complete search history.

(56) References Cited

U.S. PATENT DOCUMENTS

| 5,817,256 | A | 10/1998 | Weippert |
| 8,647,878 | B2 | 2/2014 | Weippert |
| 9,964,751 | B2 | 5/2018 | Weippert |
| 2010/0212547 | A1 | 8/2010 | Weippert |
| 2014/0355109 | A1 | 12/2014 | Weippert |

FOREIGN PATENT DOCUMENTS

| DE | 197 05 978 | 7/2013 |
| DE | 10 2013 210 113 | 12/2014 |
| DE | 10 2009 010 503 | 2/2017 |

OTHER PUBLICATIONS

English translation of German Search Reported dated Dec. 3, 2020 in German Application No. 10 2020 108 726.8, 7 pages.

*Primary Examiner* — Vishal V Vasisth
(74) *Attorney, Agent, or Firm* — Grüneberg and Myers PLLC

(57) ABSTRACT

An immersion oil for microscopy contains a) a first diester A1 based on a tricyclodecane radical K having one functional group and a first hydrocarbon derivative C1 having two functional groups, and b) a second diester A2 based on the tricyclodecane radical K having one functional group and a second hydrocarbon derivative C2 having two functional groups, where C1 and C2 are different. Methods can be used for the production of the immersion oil and for the use thereof in microscopy.

11 Claims, 1 Drawing Sheet

IMMERSION OILS HAVING LONG SERVICE LIFE

CROSS-REFERENCE TO RELATED APPLICATIONS

This application claims priority to German Patent Application No. 10 2020 108 726.8, filed Mar. 30, 2020, incorporated herein by reference.

BACKGROUND OF THE INVENTION

Field of the Invention

The present invention relates to an immersion oil for microscopy, comprising a) a first diester A1 based on a tricyclodecane radical K having one functional group and a first hydrocarbon derivative C1 having two functional groups, and b) a second diester A2 based on the tricyclodecane radical K having one functional group and a second hydrocarbon derivative C2 having two functional groups, where C1 and C2 are different, and to the use and production thereof.

Description of Related Art

Immersion oils that are produced according to DIN 8036 (June 2015) are used globally in microscopy. They are essential in this application since it is possible to increase the numerical aperture of the objective in association therewith. These objectives are frequently even explicitly calculated and optimized for use with immersion oils according to DIN 8036, such that they are only then able to exhibit their optical function. Raw materials or mixtures suitable as immersion oil according to DIN 8036 (type N and type F) must fulfil properties with regard to refractive index ($n_e^{23}$ 1.5180(5)), dispersion value or Abbe number ($v_e$ 43(4)), transmission in the visible region (N: 400-900 nm; F: 320-1100 nm), residual fluorescence (F: 0.06 mg/l (365 nm ex./450 nm em.), 1.20 mg/i (405 nm ex./485 nm); based on quinine sulfate equivalent) and viscosity (in the range of 50-1500 mPa*s, optimally 300-1000 mPa*s). Moreover, users of immersion oils in the field of microscopy have expectations in respect of yellowness value, evaporation characteristics, evolution of odour, long-term stability, homogeneity and scattering value, and the classification of the hazards to health associated with the ingredients. The users generally do not know exact numerical values, but it is found in application that the values not covered in the standard are also relevant to the user. They are additionally even a crucial factor in deciding whether an immersion oil is accepted as working medium by the user.

In order to meet regulatory regulations and substantially all the above-mentioned user expectations, great efforts have to be made in the selection and matching of the raw materials for an immersion oil. In the selection of the raw materials, it already has to be ensured that these have a minimum yellowness value, favourable evaporation characteristics, barely any evolution of odour, high long-term stability and low residual fluorescence. Moreover, no critical health risks must emanate from the raw materials. At present, partially hydrogenated polycyclic aromatics (e.g. terphenyls) and bridged fused aliphatic hydrocarbons in particular are found to be suitable. The effect of these two components in each case is that they show a balanced ratio between refractive index and dispersion, or refractive index attenuation and increased dispersion, and vice versa. The other additions that an immersion oil must contain generally serve to adjust viscosity.

In microscopy, moreover, aside from the influence of temperature, imaging quality is also influenced by parameters such as objective type, working distance, coverslip thickness and refractive index, and the refractive index of the sample examined. Since modern microscopy is developing toward ever higher resolutions, it is necessary for attainment of high image qualities for the immersion liquid used, for example an immersion oil, to be adaptable to the respective preparation temperatures. In high-resolution microscopy, it may also be necessary, in a departure from the standard refractive index according to ISO 8036, to produce immersion fluids having variable refractive index exactly adjusted to the respective examination conditions. The reference temperature in the ISO standard for immersion fluids (ISO 8036) is 23 f 0.1° C.; the refractive index $n_e$ at 546.1 nm is 1.5180 t 0.0005. However, the demands outlined above are not met by the immersion fluids available on the market that are adjusted to the standard temperature of 23° C.

DE 10 2013 210 113 A1 describes an immersion fluid for microscopy, comprising (a) an organic compound containing a saturated polycyclic hydrocarbyl radical, (b) an oligomeric or polymeric saturated acyclic hydrocarbon and (c) an alkylaromatic selected from the group consisting of alkylnaphthalene and alkylbiphenyl. The document further relates to the use of an immersion fluid in microscopy and to a process for producing the immersion fluid.

DE 10 2009 010 503 B4 describes immersion fluids of high refractive index, and a compound of high refractive index and the use thereof in microscopy.

DE 197 05 978 B4 describes an immersion oil for microscopy, comprising esters or ethers of tricyclodecane or esters or ethers of substances having base structures of tricyclodecane as the main constituent.

However, none of these documents addresses the long-term stability of an immersion oil for microscopy, which plays an important role alongside a suitable refractive index.

It has been found that the long-term stability of an immersion oil depends on the extent to which separation of the raw materials over the period of use can be prevented. In the case of constituents having a high tendency to crystallization, the formation of a crystal burden in the immersion oil has the effect that it can no longer be utilized. Only in a very time-consuming manner and with use of apparatus, for example by means of an oven, can these crystals be dissolved again by prolonged heating. However, heating has a distinctly adverse effect on other properties of the immersion oil (for example residual fluorescence), such that frequently the only option remaining is the disposal of the oil and purchase of new oil. Short service lives of immersion oils (<1 year) lead to production and storage problems for the customer, for the producer and for the supplier, and are thus undesirable and uneconomic.

In the region of extremely low residual fluorescences, a system of fused aliphatic hydrocarbons, for example in the case of TCD alcohol M, (8(9)-hydroxymethyltricyclo[$5.2.1.0^{2,6}$]decane), or TCD alcohol DM, (3(4),8(9)-dihydroxymethyltricyclo[$5.2.1.0^{2,6}$]decane), is particularly suitable since it is obtainable with a low level of complexity by distillative purification. However, especially in the case of use of a di(TCD-M) ester as the main component in the immersion oil, a disadvantageous significant tendency to crystallization is found.

SUMMARY OF THE INVENTION

The problem addressed was therefore that of providing an immersion oil having improved properties, especially with regard to long-term stability.

The invention provides an immersion oil for microscopy, comprising
   a) a first diester A1 based on a tricyclodecane radical K having one functional group and a first hydrocarbon derivative C1 having two functional groups, and
   b) a second diester A2 based on the tricyclodecane radical K having one functional group and a second hydrocarbon derivative C2 having two functional groups, where C1 and C2 are different.

The invention also includes the following embodiments:
1. Immersion oil, for microscopy, comprising
   a) a first diester A1 based on a tricyclodecane radical K having one functional group and a first hydrocarbon derivative C1 having two functional groups, and
   b) a second diester A2 based on the tricyclodecane radical K having one functional group and a second hydrocarbon derivative C2 having two functional groups,
   where C1 and C2 are different.
2. Immersion oil according to Embodiment 1, wherein the number of carbon atoms in the first hydrocarbon derivative C1 having two functional groups and in the second hydrocarbon derivative C2 having two functional groups differs by at least one carbon atom.
3. Immersion oil according to Embodiments 1 or 2, wherein the tricyclodecane radical K having one functional group is selected from the group consisting of:

tricyclo[5.2.1.0$^{2,6}$]decane-2-carboxylic acid

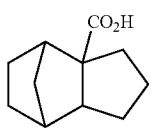

tricyclo[5.2.1.0$^{2,6}$]decane-4-carboxylic acid (TCD carboxylic acid S)

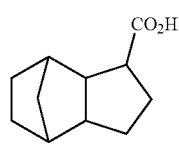 [SMILES: O=C(O)C1CCC2C3CCC(C3)C12]

tricyclo[5.2.1.0$^{2,6}$]decane-8-carboxylic acid (TCD carboxylic acid S)

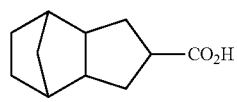

tricyclo[5.2.1.0$^{2,6}$]decane-9-carboxylic acid

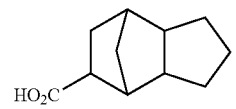 [SMILES: O=C(O)C1CC2CC1C1CCCC21]

tricyclo[5.2.1.0$^{2,6}$]decane-9-carboxylic acid

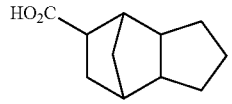

3-hydroxymethyltricyclo[5.2.1.0$^{2,6}$]decane

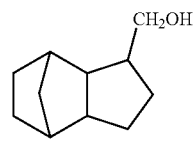

4-hydroxymethyltricyclo[5.2.1.0$^{2,6}$]decane

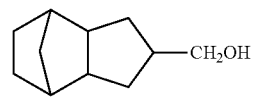 [SMILES: OCC1CC2C3CCC(C3)C2C1]

8-hydroxymethyltricyclo[5.2.1.0$^{2,6}$]decane (TCD alcohol M)

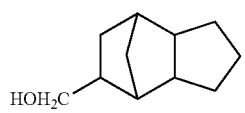

9-hydroxymethyltricyclo[5.2.1.0$^{2,6}$]decane

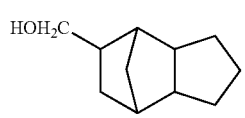 [SMILES: OCC1CC2CC1C1CCCC21]

3-hydroxytricyclo[5.2.1.0$^{2,6}$]decane

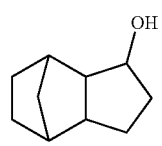 [SMILES: OC1CCC2C3CCC(C3)C12]

4-hydroxytricyclo[5.2.1.0$^{2,6}$]decane

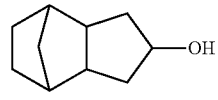 [SMILES: OC1CC2C3CCC(C3)C2C1]

8-hydroxytricyclo[5.2.1.0²,⁶]decane

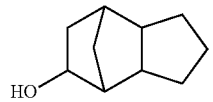

9-hydroxytricyclo[5.2.1.0²,⁶]decane

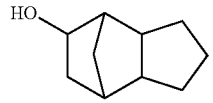

8-hydroxytricyclo[5.2.1.0²,⁶]dec-3-ene (TCD alcohol E)

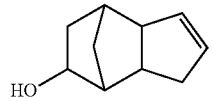

9-hydroxytricyclo[5.2.1.0²,⁶]dec-3-ene (TCD alcohol E)

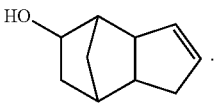

4. Immersion oil according to any of Embodiments 1 to 3, wherein the tricyclodecane radical K having one functional group is selected from the group consisting of:

3-hydroxymethyltricyclo[5.2.1.0²,⁶]decane

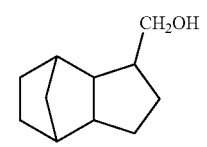 [SMILES: OCC1CCC2C3CCC(C3)C12]

4-hydroxymethyltricyclo[5.2.1.0²,⁶]decane

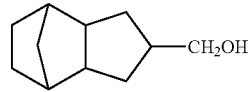 [SMILES: OCC1CC2C3CCC(C3)C2C1]

8-hydroxymethyltricyclo[5.2.1.0²,⁶]decane (TCD alcohol M)

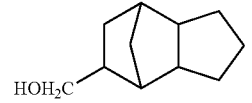 [SMILES: OCC1CC2CC1C1CCCC21]

9-hydroxymethyltricyclo[5.2.1.0²,⁶]decane

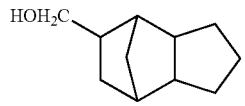 [SMILES: OCC1CC2CC1C1CCCC21]

3-hydroxytricyclo[5.2.1.0²,⁶]decane

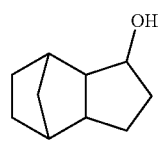 [SMILES: OC1CCC2C3CCC(C3)C12]

4-hydroxytricyclo[5.2.1.0²,⁶]decane

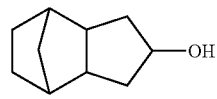

8-hydroxytricyclo[5.2.1.0²,⁶]decane

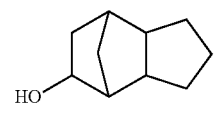 [SMILES: OC1CC2CC1C1CCCC21]

9-hydroxytricyclo[5.2.1.0²,⁶]decane

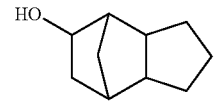

8-hydroxytricyclo[5.2.1.0²,⁶]dec-3-ene (TCD alcohol E)

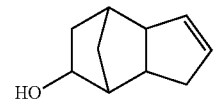 [SMILES: OC1CC2CC1C1CC=CC21]

9-hydroxytricyclo[5.2.1.0²,⁶]dec-3-ene (TCD alcohol E)

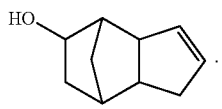

5. Immersion oil according to any of Embodiments 1 to 4, comprising:
   a) 15-85% by weight of the first diester A1 based on a tricyclodecane radical K having one functional group and a first hydrocarbon derivative C1 having two functional groups, and b) 15-85% by weight of the second diester A2 based on the tricyclodecane radical K having one functional group and a second hydrocarbon derivative C2 having two functional groups.

6. Immersion oil according to any of Embodiments 1 to 5, wherein the amount of diesters A1 and A2 satisfies the following conditions:
   (i) % by mass(A1)=% by mass(A1)$^E$±5% by mass,
   (ii) % by mass(A2)=% by mass(A2)$^E$±5% by mass,
   where % by mass(A1)$^E$ and % by mass(A2)$^E$ correspond to the percentages by mass of A1 and A2 at the eutectic point in a phase diagram of a mixture of A1 and A2.

7. Immersion oil according to any of Embodiments 1 to 6, wherein the dispersion value is within a range from 49±2 to 47±2.

8. Immersion oil according to any of Embodiments 1 to 7, wherein transmission in the visible region is more than 70% at wavelengths greater than 350 nm.

9. Immersion oil obtainable by
   (a) reacting
   (i) a tricyclodecane radical K having one functional group and a first hydrocarbon derivative C1 having two functional groups,
   (ii) the tricyclodecane radical K having one functional group and a second hydrocarbon derivative C2 having two functional groups,
   where C1 and C2 are different, in a spatially unseparated one-pot reaction and (b) workup, distillative workup or activated carbon filtration of the reaction product from (a).

10. Use of an immersion oil according to any of Embodiments 1 to 9 in microscopy.

11. Process for producing an immersion oil according to any of Embodiments 1 to 9, comprising the following steps:
    i) providing a first diester A1 and a second diester A2 as mixture M,
    ii) optionally providing further constituents and
    iii) mixing the first diester A1 and the second diester A2 with any further constituents.

12. Method according to Embodiment 11, wherein step i) is conducted by the providing of a mixture M consisting of a first diester A1 and a second diester A2, wherein the providing of the mixture M comprises the following steps:
    iv) preparing a solution of a first hydrocarbon derivative C1 having two functional groups and a second hydrocarbon derivative C2 having two functional groups in a solvent,
    v) adding a tricyclodecane radical K having one functional group, and
    vi) optionally heating the reaction mixture and optionally adding an esterification catalyst.

13. Method according to Embodiment 12, wherein step vi) is followed by performance of the steps of
    vii) removing the crude product obtained and
    viii) optionally purifying the crude product obtained.

DETAILED DESCRIPTION OF THE INVENTION

Figure 1A:
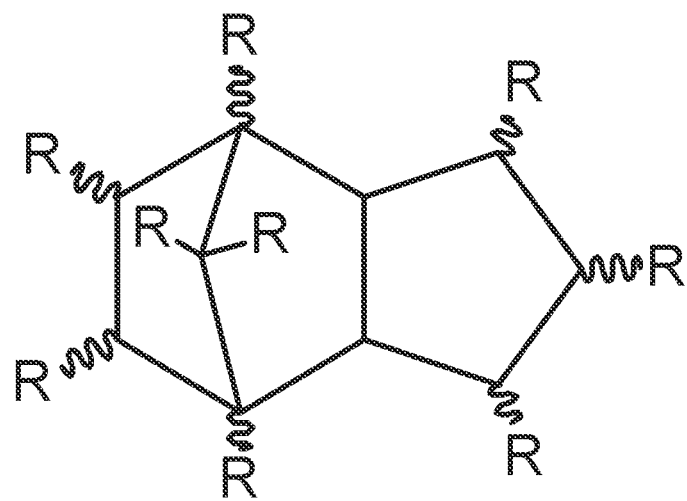
FIG. 1A shows an example of a TCD monomer.

Ideally, the use of two different diesters having a similar chemical structure pattern that prevents mutual crystallization can assure appropriate long-term stability. It is known that molecules become oriented in the course of crystallization so as to be in the most favourable orientation relative to other molecules. If the two partners involved have the same structure, the two molecules can "dock onto" one another with an exact fit and assume very short distances from one another. This process continues, and crystals are formed. If structurally related molecules are present in a mixture, it is possible for orientations to develop, but "docking" cannot take place. This gives rise to a dynamic equilibrium between the two types of molecule, which are constantly displaced again from the crystallization sites of the respective other type of molecule. If the structural relationship between molecular species involved is only weak, there will be no orientation of the two types of molecule with respect to one another either. What then occurs is separate crystallization of the individual components, since, in spite of the mixing of different chemical structure patterns, there is no longer any displacement from crystallization sites.

An immersion oil in the context of the present invention is advantageously a fluid that enhances resolution in light microscopy (UV/vis). More particularly, an immersion oil in the context of the present invention is a fluid which is an immersion fluid according to DIN 8036 (June 2015).

A hydrocarbon in the context of the invention is an organic chemical compound consisting of carbon and hydrogen. In accordance with the general IUPAC definition, "aliphatic" is understood to mean a non-aromatic organic chemical compound.

In the context of the present invention, the term "hydrocarbon derivative" may be understood to mean a hydrocarbon having heteroatoms.

The expression "diester based on" a tricyclodecane radical K having one functional group and a first/second hydrocarbon derivative C1/C2 having two functional groups is based on a diester that has formed from components K and C1/C2 by a reaction on account of the functional groups. Ideally, this reaction proceeds via a condensation reaction, meaning that a small molecule, for example water, is eliminated. The expression "one functional group" is understood to mean a chemical structural unit that can react with another chemical group, for example by means of an addition reaction or a condensation reaction. The expression "two functional groups" is understood to mean a structural unit that can react with two other chemical groups, for example by means of a condensation reaction. The "two functional groups" may also take the form, for example, of an anhydride.

Preferably, the number of carbon atoms in the first hydrocarbon derivative C1 having two functional groups and in the second hydrocarbon derivative C2 having two functional groups differs by at least one carbon atom, very preferably by two to six and most preferably by two carbon atoms. This results in two different diesters having a similar chemical structure pattern, optionally substituted by appropriate functional groups rather than a hydrogen atom, wherein mutual crystallization is constrained.

Figure 1B:
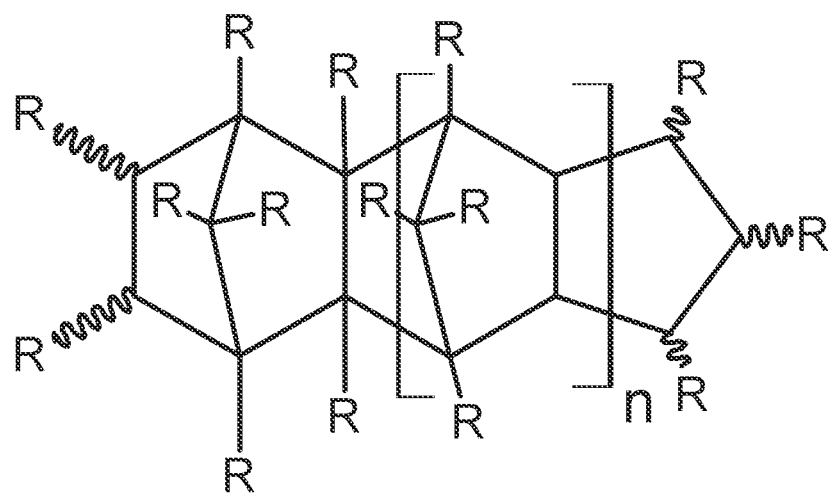
FIG. 1B shows an example of a TCD oligomer or polymer.

There are many possible substances having a base structure of tricyclodecane, the esters of which are possible immersion oils according to the invention. A tricyclodecane radical in the context of the present invention may be understood to mean structural formulae of those substances according to FIGS. 1A and 1B. These may be a TCD monomer (FIG. 1A) or a TCD oligomer or polymer (see FIG. 1B) in which the ring structure enclosed by square brackets in FIG. 1B occurs in n repetitions. One or more of the hydrogen atoms in the TCD skeleton may also, as indicated in FIG. 1A, each be replaced by a substituent R. Examples of suitable substituents R are —CH$_2$—CH$_2$OH, —CH$_2$OH and —OH. The replacement of the hydrogen atoms by R radicals preferably has only a minor influence on the physical properties that are important for immersion oils.

The tricyclodecane radical K having one functional group has preferably 10-18, especially 10-14, carbon atoms. More preferably, the tricyclodecane radical K is tricyclo[5.2.1.0$^{2,6}$]decanyl (TCD). Tricyclodecane and some derivatives thereof are available on the industrial scale because they can be obtained from the dimer of cyclopentadiene.

Tricyclodecane-based immersion oils are particularly suitable in the region of low residual fluorescences. Therefore, the tricyclodecane radical K having one functional group is preferably selected from the group consisting of:

tricyclo[5.2.1.0$^{2,6}$]decane-2-carboxylic acid

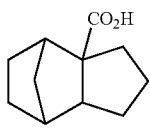

tricyclo[5.2.1.0$^{2,6}$]decane-3-carboxylic acid (TCD carboxylic acid S)

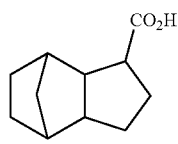 [SMILES: O=C(O)C1CCC2C3CCC(C3)C12]

tricyclo[5.2.1.0$^{2,6}$]decane-4-carboxylic acid (TCD carboxylic acid S)

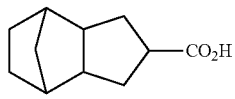 [SMILES: O=C(O)C1CC2C3CCC(C3)C2C1]

tricyclo[5.2.1.0$^{2,6}$]decane-8-carboxylic acid

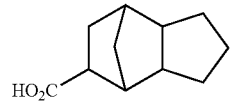 [SMILES: O=C(O)C1CC2CC1C1CCCC21]

tricyclo[5.2.1.0$^{2,6}$]decane-9-carboxylic acid

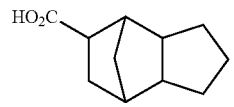 [SMILES: O=C(O)C1CC2CC1C1CCCC21]

3-hydroxymethyltricyclo[5.2.1.0$^{2,6}$]decane

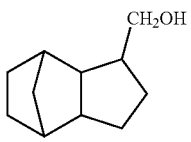

4-hydroxymethyltricyclo[5.2.1.0$^{2,6}$]decane

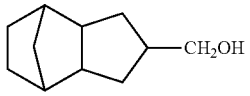

8-hydroxymethyltricyclo[5.2.1.0$^{2,6}$]decane (TCD alcohol M)

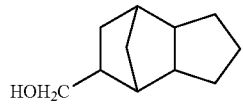

9-hydroxymethyltricyclo[5.2.1.0$^{2,6}$]decane

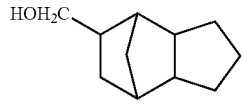 [SMILES: OCC1CC2CC1C1CCCC21]

3-hydroxytricyclo[5.2.1.0$^{2,6}$]decane

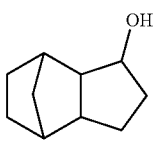 [SMILES: OC1CCC2C3CCC(C3)C12]

4-hydroxytricyclo[5.2.1.0$^{2,6}$]decane

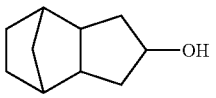

8-hydroxytricyclo[5.2.1.0$^{2,6}$]decane

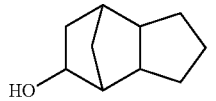 [SMILES: OC1CC2CC1C1CCCC21]

9-hydroxytricyclo[5.2.1.0$^{2,6}$]decane

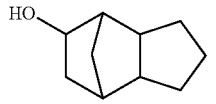

8-hydroxytricyclo[5.2.1.0$^{2,6}$]dec-3-ene (TCD alcohol E)

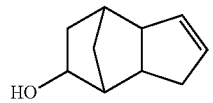

9-hydroxytricyclo[5.2.1.0$^{2,6}$]dec-3-ene HO (TCD alcohol E)

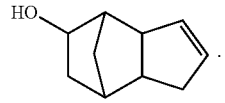

The tricyclodecane radical K having one functional group is more preferably selected from the group consisting of:

3-hydroxymethyltricyclo[5.2.1.0$^{2,6}$]decane

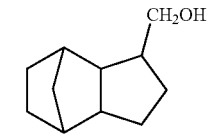 [SMILES: OCC1CCC2C3CCC(C3)C12]

4-hydroxymethyltricyclo[5.2.1.0$^{2,6}$]decane

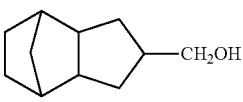 [SMILES: OCC1CC2C3CCC(C3)C2C1]

8-hydroxymethyltricyclo[5.2.1.0$^{2,6}$]decane (TCD alcohol M)

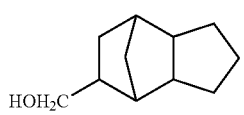

9-hydroxymethyltricyclo[5.2.1.0$^{2,6}$]decane

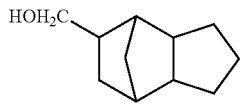

3-hydroxytricyclo[5.2.1.0$^{2,6}$]decane

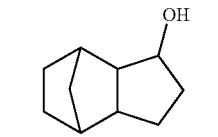 [SMILES: OC1CCC2C3CCC(C3)C12]

4-hydroxytricyclo[5.2.1.0$^{2,6}$]decane

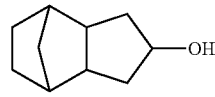 [SMILES: OC1CC2C3CCC(C3)C2C1]

8-hydroxytricyclo[5.2.1.0$^{2,6}$]decane

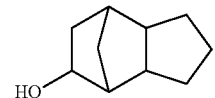

9-hydroxytricyclo[5.2.1.0$^{2,6}$]decane

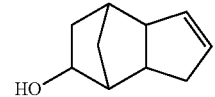

8-hydroxytricyclo[5.2.1.0$^{2,6}$]dec-3-ene (TCD alcohol E)

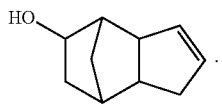

and 9-hydroxytricyclo[5.2.1.0$^{2,6}$]dec-3-ene (TCD alcohol E)

In order to advantageously constrain crystallization, the diesters A1 and A2 may be present in a particular ratio. Advantageously, the immersion oil according to the invention comprises:

a) 15-85% by weight of the first diester A1 based on a tricyclodecane radical K having one functional group and a first hydrocarbon derivative C1 having two functional groups, and b) 15-85% by weight of the second diester A2 based on the tricyclodecane radical K having one functional group and a second hydrocarbon derivative C2 having two functional groups.

Most preferably, the immersion oil according to the invention comprises:

a) 40-60% by weight of the first diester A1 based on a tricyclodecane radical K having one functional group and a first hydrocarbon derivative C1 having two functional groups, and b) 40-60% by weight of the second diester A2 based on the tricyclodecane radical K having one functional group and a second hydrocarbon derivative C2 having two functional groups.

Most preferably, the amount of diesters A1 and A2 satisfies the following conditions:

(i) % by mass(A1)=% by mass(A1)$^E$±5% by mass,
(ii) % by mass(A2)=% by mass(A2)$^E$±5% by mass, especially
(iii) % by mass(A1)+% by mass(A2)=100% by mass, where % by mass(A1)E and % by mass(A2)E correspond to the percentages by mass of A1 and A2 at the eutectic point in a phase diagram of a mixture of A1 and A2.

Diester A1

The first diester A1 based on a tricyclodecane radical K having one functional group and a first hydrocarbon derivative C1 having two functional groups is preferably an ester of tricyclodecane alcohols.

Preferred tricyclodecane alcohols are especially hydroxymethyltricyclo[5.2.1.0$^{2,6}$]decane, for example 8-hydroxymethyltricyclo[5.2.1.0$^{2,6}$]decane and 9-hydroxymethyltricyclo[5.2.1.0$^{2,6}$]decane.

Particular preference is given to TCD alcohol M (8-hydroxymethyltricyclo[5.2.1.0$^{2,6}$]decane), which is available on the industrial scale, sold, for example, by Oxea GmbH, Oberhausen, Germany.

The first diester A1 based on a tricyclodecane radical K having one functional group and a first hydrocarbon derivative C1 having two functional groups is preferably an ester of dicarboxylic acids. Examples of suitable dicarboxylic acids are phthalic acid, isophthalic acid, terephthalic acid, hexahydrophthalic acid, hexahydroisophthalic acid, hexahydroterephthalic acid, malonic acid, succinic acid, maleic acid, glutaric acid, adipic acid or sebacic acid. Particular preference is given to succinic acid.

Esterification can be accomplished using the customary esterification methods that are known to the person skilled in the art.

The first diester A1 based on a tricyclodecane radical K having one functional group and a first hydrocarbon derivative C1 having two functional groups can also preferably be described by the following formula (I):

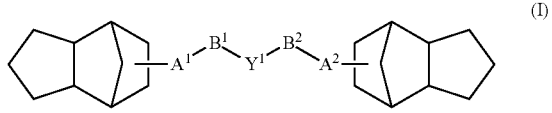

(I)

in which
A$^1$ and A$^2$ are independently selected from the group consisting of —O—C(O)—, —C(O)O—, —O—, methylene and ethylene,
B$^1$ and B$^2$ are independently selected from the group consisting of C$_1$-C$_{20}$-alkylene, C$_1$-C$_{20}$-haloalkylene, C$_1$-C$_{12}$-alkoxyalkylene. C$_1$-C$_6$-cyanoalkylene, C$_3$-C$_{18}$-alkenylene, C$_3$-C$_{18}$-haloalkenylene, C$_3$- or C$_4$-alkynylene. C$_3$-C$_{12}$-cycloalkylene, C$_4$-C$_{12}$-cycloalkylalkylene, —O—C(O)—, —C(O)O—, C$_3$-C$_{16}$-alkoxycarbonylalkylene and optionally substituted C$_7$-C$_{20}$-aralkylene, and
Y$^1$ is selected from the group consisting of methylene, ethylene, propylene, butylene, pentylene, hexylene and substituted or unsubstituted C$_8$-C$_{12}$-alkylenearyl.

Preferably, B$^1$ and B$^2$ are independently selected from the group consisting of methylene, ethylene, n-propylene, iso-propylene, n-butylene, isobutylene, sec-butylene, tert-butylene, n-pentylene, n-hexylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene, —O—C(O)— and —C(O)O—.

Most preferably, B$^1$ and B$^2$ are independently selected from the group consisting of methylene, ethylene, n-propylene, n-butylene, —O—C(O)— and —C(O)O—.

The first diester A1 based on a tricyclodecane radical K having one functional group and a first hydrocarbon derivative C$_1$ having two functional groups can also preferably be described by the following formula (Ia):

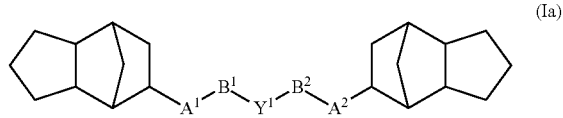

(Ia)

in which
A$^1$ and A$^2$ are independently selected from the group consisting of —O—C(O)—, —C(O)O—. —O—, methylene and ethylene,
B$^1$ and B$^2$ are independently selected from the group consisting of C$_1$-C$_{20}$-alkylene, C$_1$-C$_{20}$ haloalkylene. —O—C(O)—. —C(O)O—, and C$_1$-C$_{12}$-alkoxyalkylene, especially O—C(O)— and —C(O)O—.
Y$^1$ is selected from the group consisting of methylene, ethylene, propylene, butylene, pentylene, hexylene and substituted or unsubstituted C$_8$-alkylenearyl.

Very particular preference is given to di(methyltricyclo[5.2.1.0$^{2,6}$]decane) succinate as the diester A1.

Diester A2

The second diester A2 based on a tricyclodecane radical K having one functional group and a second hydrocarbon derivative C2 having two functional groups is preferably an ester of tricyclodecane alcohols.

Preferred tricyclodecane alcohols are especially hydroxymethyltricyclo[5.2.1.0$^{2,6}$]decane, for example 8-hydroxymethyltricyclo[5.2.1.0$^{2,6}$]decane and 9-hydroxymethyltricyclo[5.2.1.0$^{2,6}$]decane.

Particular preference is given to TCD alcohol M (=8-hydroxymethyltricyclo[5.2.1.0$^{2,6}$]decane), which is available on the industrial scale, sold, for example, by Oxea GmbH, Oberhausen, Germany.

The second diester A2 based on a tricyclodecane radical K having one functional group and a second hydrocarbon derivative C2 having two functional groups is preferably an ester of dicarboxylic acids. Examples of suitable dicarboxylic acids are phthalic acid, isophthalic acid, terephthalic acid, hexahydrophthalic acid, hexahydroisophthalic acid, hexahydroterephthalic acid, malonic acid, succinic acid, maleic acid, glutaric acid, adipic acid or sebacic acid. Particular preference is given to adipic acid.

Esterification can be accomplished using the customary esterification methods that are known to the person skilled in the art.

The second diester A2 based on a tricyclodecane radical K having one functional group and a second hydrocarbon derivative C2 having two functional groups can also preferably be described by the following formula (II):

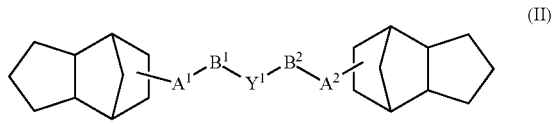

(II)

in which
- $A^1$ and $A^2$ are independently selected from the group consisting of —O—C(O)—, —C(O)O—, —O—, methylene and ethylene,
- $B^1$ and $B^2$ are independently selected from the group consisting of $C_1$-$C_{20}$-alkylene, $C_1$-$C_{20}$-haloalkylene, $C_1$-$C_{12}$-alkoxyalkylene, $C_1$-$C_6$-cyanoalkylene, $C_3$-$C_{18}$-alkenylene, $C_3$-$C_{18}$-haloalkenylene, $C_3$- or $C_4$-alkynylene, $C_3$-$C_{12}$-cycloalkylene, $C_4$-$C_{12}$-cycloalkylalkylene, —O—C(O)—, —C(O)O—, $C_3$-$C_{16}$-alkoxycarbonylalkylene and optionally substituted $C_7$-$C_{20}$-aralkylene, and
- $Y^2$ is selected from the group consisting of methylene, ethylene, propylene, butylene, pentylene, hexylene and substituted or unsubstituted $C_8$-$C_{12}$-alkylenearyl.

Preferably, $B^1$ and $B^2$ are independently selected from the group consisting of methylene, ethylene, n-propylene, isopropylene, n-butylene, isobutylene, sec-butylene, tert-butylene, n-pentylene, n-hexylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene, —O—C(O)— and —C(O)O—.

Most preferably. $B^1$ and $B^2$ are independently selected from the group consisting of methylene, ethylene, n-propylene, n-butylene, —O—C(O)— and —C(O)O—.

The second diester A2 based on a tricyclodecane radical K having one functional group and a second hydrocarbon derivative C2 having two functional groups can also preferably be described by the following formula (IIb):

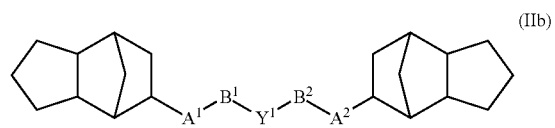

(IIb)

in which
- $A^1$ and $A^2$ are independently selected from the group consisting of —O—C(O)—, —C(O)O—, —O—, methylene and ethylene,
- $B^1$ and $B^2$ are independently selected from the group consisting of $C_1$-$C_{20}$-alkylene, $C_1$-$C_{20}$-haloalkylene, —O—C(O)—, —C(O)O— and $C_1$-$C_{12}$-alkoxyalkenyl, especially O—C(O)— and —C(O)O—,
- $Y^2$ is selected from the group consisting of methylene, ethylene, propylene, butylene, pentylene, hexylene and substituted or unsubstituted $C_8$-alkylenearyl.

Very particular preference is given to di(methyltricyclo[5.2.1.0$^{2,6}$]decane) adipate as the diester A2.

Most preferably, the immersion oil according to the invention for microscopy comprises
a) a first diester A1 based on a tricyclodecane radical K having one functional group and a first hydrocarbon derivative C1 having two functional groups, represented by the following formula (IIIa):

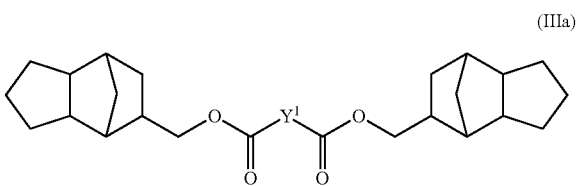

(IIIa)

in which
- $Y^1$ is selected from the group consisting of methylene, ethylene, propylene, butylene, pentylene, hexylene, heptylene and octylene,
b) a second diester A2 based on the tricyclodecane radical K having one functional group and a second hydrocarbon derivative C2 having two functional groups, represented by the following formula (IIIb):

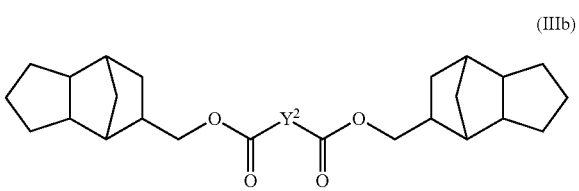

(IIIb)

in which
- $Y^1$ is selected from the group consisting of methylene, ethylene, propylene, butylene, pentylene, hexylene, heptylene, octylene, nonylene and decylene,
- where $Y^1$ and $Y^2$ are different.

Most preferably, the immersion oil according to the invention for microscopy comprises
a) a first diester A1 based on a tricyclodecane radical K having one functional group and a first hydrocarbon derivative C1 having two functional groups, represented by the following formula (IVa):

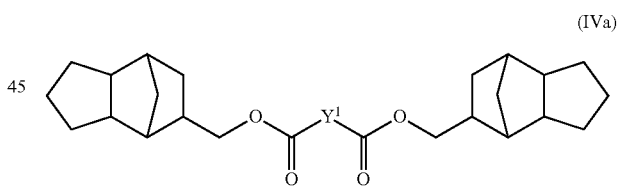

(IVa)

in which
- $Y^1$ is selected from the group consisting of methylene, ethylene and propylene,
b) a second diester A2 based on the tricyclodecane radical K having one functional group and a second hydrocarbon derivative C2 having two functional groups, represented by the following formula (IVb):

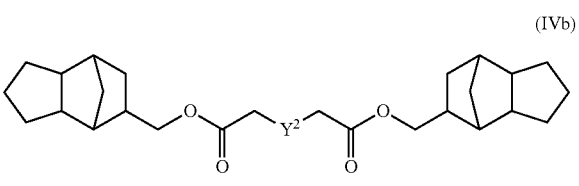

(IVb)

in which
Y² is selected from the group consisting of ethylene, propylene, butylene, pentylene and hexylene.

Immersion Oil

In the adjustment of the parameters of refractive index, dispersion (expressed as the Abbe number) and viscosity, the diesters A1 and A2 (mixture M) have the function of providing a low dispersion (high Abbe number) coupled with a simultaneously relatively high refractive index. The diesters serve primarily to increase the viscosity of the immersion oil, which is important particularly at relatively high working temperatures. An excessively mobile immersion oil has the disadvantage that it runs off the microscope slide too quickly and hence optical contact between objective and preparation cannot be maintained for a sufficiently long period. In the case of an excessively viscous immersion oil, by contrast, troublesome bubbles can arise in the immersion oil on application to the preparation.

The refractive index, dispersion and viscosity of the immersion oil according to the invention can be set to desired values for a particular working temperature. In particular, it is possible to establish a refractive index $n_e$ at the desired working temperature in the range of 1.5100-1.5500, preferably 1.5180-1.5300. The Abbe number at the desired working temperature is in the range of 39-47, and the kinematic viscosity is adjustable between 150-1500 mm²/s. A preferred working temperature is 0-50° C., especially 0-22° C. and 24-50° C.

Preferably, in the immersion oil according to the invention, the dispersion value is within a range from 39±2 to 47±2, most preferably within a range from 42±2 to 46±2.

An important property of an immersion oil is the UV/vis transparency. Advantageously, in the immersion oil according to the invention, transmittance in the visible region is more than 70% at wavelengths greater than 350 nm and preferably more than 90% at wavelengths greater than 400 nm (N), and more than 90% at wavelengths greater than 365 nm (F). (N) is the type N immersion oil, and (F) the type F immersion oil.

Particular preference is given to an immersion oil for microscopy comprising
a) a first diester A1, represented by the following formula (Va):

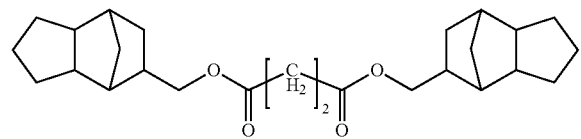

b) a second diester A2, represented by the following formula (Vb):

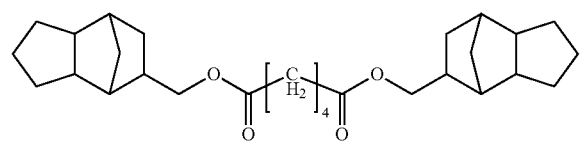

Very particular preference is given to an immersion oil for microscopy comprising
a) 40-60% by weight of the first diester A1, represented by the following formula (Va):

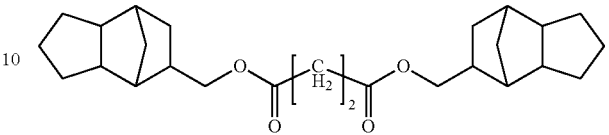

b) 40-60% by weight of the second diester A2, represented by the following formula (Vb):

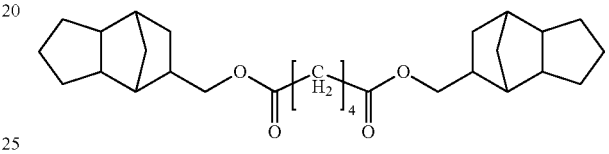

where the sum total of the amount of A1 and the amount of A2 is 100% by weight.

In a further embodiment, the invention relates to an immersion oil obtainable by
(a) reacting (i) a tricyclodecane radical K having one functional group and a first hydrocarbon derivative C1 having two functional groups, (ii) the tricyclodecane radical K having one functional group and a second hydrocarbon derivative C2 having two functional groups, where C1 and C2 are different, in a spatially unseparated one-pot reaction and
(b) workup, distillative workup or activated carbon filtration, and preferably formulation, of the reaction product from (a).

The invention preferably relates to an immersion oil obtainable by
(a) simultaneously reacting
(i) a tricyclodecane radical K having one functional group and a first hydrocarbon derivative C1 having two functional groups to give the product, represented by the following formula (Ia):

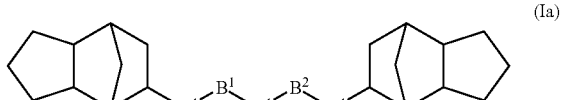

in which
A¹ and A² are independently selected from the group consisting of
—O—C(O)—, —C(O)O—, —O—, methylene and ethylene,
B¹ and B² are independently selected from the group consisting of $C_1$-$C_{20}$-alkylene, $C_1$-$C_{20}$-haloalkylene, —O—C(O)—, —C(O)O— and $C_1$-$C_{12}$-alkoxyalkylene.
Y¹ is selected from the group consisting of methylene, ethylene, propylene, butylene, pentylene, hexylene and substituted or unsubstituted $C_8$-alkylarylene, and
(ii) the tricyclodecane radical K having one functional group and a second hydrocarbon derivative C2 having two functional groups to give the product, represented by the following formula (Iib):

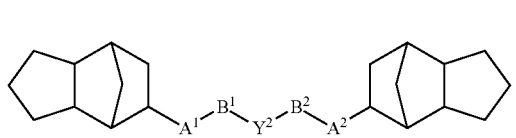

(IIb)

in which
  $A^1$ and $A^2$ are independently selected from the group consisting of
    —O—C(O)—. —C(O)O—, —O—, methylene and ethylene,
  $B^1$ and $B^2$ are independently selected from the group consisting of $C_1$-$C_2M$-alkylene, $C_1$-$C_{20}$-haloalkylene, —O—C(O)—, —C(O)O— and $C_1$-$C_{12}$-alkoxyalkylene,
  $Y^2$ is selected from the group consisting of methylene, ethylene, propylene, butylene, pentylene, hexylene and substituted or unsubstituted $C_8$-alkylenearyl, where $C_1$ and $C_2$ are different, and
(b) workup and distillative purification of the reaction product from (a).

A workup in step (b) may comprise ending of the reaction, an extraction step and possible drying of the product obtained.

The product obtained after the distillative purification from step (b) may preferably be subjected to further purification steps, for example filtration or extraction.

A simultaneous reaction is preferably understood to mean that the components to be converted are simultaneously reacted with one another, being present in the same reaction apparatus in the conversion.

The invention more preferably relates to an immersion oil obtainable by
(a) simultaneously reacting
  (i) 40-70 mol % of a tricyclodecane radical K having one functional group and 10-30 mol % of a first hydrocarbon derivative C1 having two functional groups to give the product, represented by the following formula (Ia):

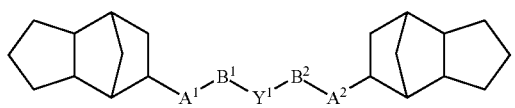

(Ia)

in which
  $A^1$ and $A^2$ are independently selected from the group consisting of
    —O—C(O)—, —C(O)O—, —O—, methylene and ethylene,
  $B^1$ and $B^2$ are independently selected from the group consisting of $C_1$-$C_{20}$-alkylene, $C_1$-$C_{20}$-haloalkylene, —O—C(O)—, —C(O)O— and $C_1$-$C_{12}$-alkoxyalkylene,
  $Y^1$ is selected from the group consisting of methylene, ethylene, propylene, butylene, pentylene, hexylene and substituted or unsubstituted Ca-alkylenearyl, and
(ii) 40-70 mol % of a tricyclodecane radical K having one functional group and 5-25 mol % of a second hydrocarbon derivative C2 having two functional groups to give the product, represented by the following formula (IIb):

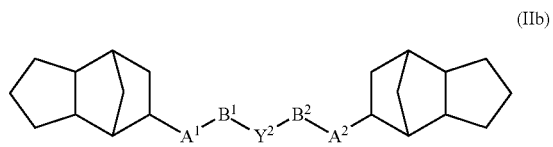

(IIb)

in which
  $A^1$ and $A^2$ are independently selected from the group consisting of
    —O—C(O)—. —C(O)O—, —O—, methylene and ethylene,
  $B^1$ and $B^2$ are independently selected from the group consisting of $C_1$-$C_2M$-alkylene, $C_1$-$C_{20}$-haloalkylene. —O—C(O)—, —C(O)O— and $C_1$-$C_{12}$-alkoxyalkylene,
  $Y^2$ is selected from the group consisting of methylene, ethylene, propylene, butylene, pentylene, hexylene and substituted or unsubstituted $C_8$-alkylenearyl, where $C_1$ and $C_2$ are different, and
(b) distillative purification of the reaction product from (a).

The product obtained after the distillative purification from step (b) may preferably be subjected to further purification steps, for example filtration or extraction.

The invention further relates to the use of an immersion oil according to the invention in microscopy. Especially for light and fluorescence microscopy.

The invention more preferably relates to the use of an immersion oil obtainable by
(a) simultaneously reacting
  (i) a tricyclodecane radical K having one functional group and a first hydrocarbon derivative C1 having two functional groups to give the product, represented by the following formula (Ia):

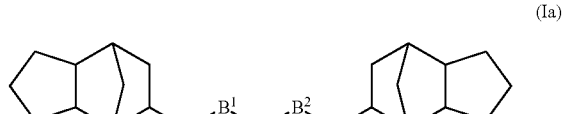

(Ia)

in which
  $A^1$ and $A^2$ are independently selected from the group consisting of
    —O—C(O)—. —C(O)O—, —O—, methylene and ethylene,
  $B^1$ and $B^2$ are independently selected from the group consisting of $C_1$-$C_{20}$-alkylene, $C_1$-$C_{20}$-haloalkylene. —O—C(O)—, —C(O)O— and $C_1$-$C_{12}$-alkoxyalkylene,
  $Y^1$ is selected from the group consisting of methylene, ethylene, propylene, butylene, pentylene, hexylene and substituted or unsubstituted $C_8$-alkylenearyl,
and
(ii) the tricyclodecane radical K having one functional group and a second hydrocarbon derivative C2 having two functional groups to give the product, represented by the following formula (IIb):

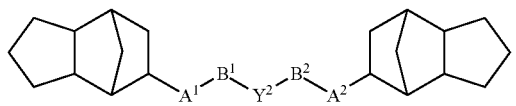
(IIb)

in which
- $A^1$ and $A^2$ are independently selected from the group consisting of
—O—C(O)—, —C(O)O—, —O—, methylene and ethylene,
- $B^1$ and $B^2$ are independently selected from the group consisting of $C_1$-$C_{20}$-alkylene, $C_1$-$C_{20}$-haloalkylene, —O—C(O)—, —C(O)O— and $C_1$-$C_{12}$-alkoxyalkylene.
- $Y^2$ is selected from the group consisting of methylene, ethylene, propylene, butylene, pentylene, hexylene and substituted or unsubstituted $C_8$-alkylenearyl, where C1 and C2 are different, and (b) distillative purification of the reaction product from (a), for microscopy.

The invention further relates to a process for producing an immersion oil, comprising the following steps:
i) providing a first diester A1 and a second diester A2 as mixture M.
ii) optionally providing further constituents and
iii) mixing the first diester A1 and the second diester A2 with any further constituents.

In the process according to the invention, step i) is preferably conducted by the providing of a mixture M consisting of a first diester A1 and a second diester A2, wherein the providing of the mixture M comprises the following steps:
iv) preparing a solution of a first hydrocarbon derivative C1 having two functional groups and a second hydrocarbon derivative C2 having two functional groups in a solvent,
v) adding a tricyclodecane radical K having one functional group, and
vi) optionally heating the reaction mixture and optionally adding an esterification catalyst.

In the process according to the invention, preference is likewise given to performing, after step vi), the steps of
vii) removing the crude product obtained and
viii) optionally purifying the crude product obtained.

The production of the mixture of two di(TCD-M) esters (A1 and A2) is particularly advantageous, cost-efficient and time-saving when these are synthesized directly in one step together from the dicarboxylic acids (C1 and C2) and TCD alcohol M (K). The dicarboxylic acids (e.g. adipic acid and succinic acid) are initially charged in the eutectically optimal ratio together with TCD alcohol M and solvent in the reactor, and subjected to a customary esterification reaction by means of PTSA (para-toluenesulfonic acid). The advantage of this reaction regime is that no crystalline products (can) form, and further processing and distillative purification of the reaction mixture is possible by pumped circulation. A further advantage is the common (simultaneous) synthesis of the diesters, and that these have high long-term stability after preparation.

Preparation of TCD Alcohol M Mixed Esters

Examples 1 to 4

Provision of a solution of carboxylic acid 1 and carboxylic acid 2 in cyclohexane, addition of TCD alcohol M, heating, then addition of para-toluenesulfonic acid (PTSA). The type of carboxylic acids used and the amounts used are shown in Table 1. Water of reaction is obtained, and this is used to monitor the progress of the reaction. After the reaction has ended, the mixture is cooled, and the solution is washed repeatedly with water or salt solutions (e.g. sodium chloride solution). The crude fraction is freed of the cyclohexane, and the product is used directly or first purified by distillation and/or by activated carbon filtration.

TABLE I

| Example 1 | | |
|---|---|---|
| Carboxylic acid 1 | adipic acid | 22.60 mol |
| Carboxylic acid 2 | succinic anhydride | 6.00 mol |
| TCD alcohol M | | 63.85 mol |
| PTSA | | 0.0147 mol |
| Cyclohexane | | 6.5 l |
| Example 2 | | |
| Carboxylic acid 1 | adipic acid | 198.6 mol |
| Carboxylic acid 2 | succinic acid | 169.5 mol |
| TCD alcohol M | | 795.2 mol |
| PTSA | | 1.5 mol |
| Cyclohexane | | 50 l |
| Example 3 | | |
| Carboxylic acid 1 | adipic acid | 191.8 mol |
| Carboxylic acid 2 | succinic acid | 156.8 mol |
| TCD alcohol M | | 771.1 mol |
| PTSA | | 1.5 mol |
| Cyclohexane | | 50 l |
| Example 4 | | |
| Carboxylic acid 1 | adipic acid | 198.6 mol |
| Carboxylic acid 2 | succinic acid | 161.0 mol |
| TCD alcohol M | | 783.1 mol |
| PTSA | | 1.5 mol |
| Cyclohexane | | 50 l |

Table 11 reports the physical properties that are important for immersion oils for some preferred di(TCD methylol) esters. Essential factors for excellent suitability of aliphatic di(TCD methylol) esters as the main constituent of immersion oils are refractive index $n_e$>1.5 and simultaneously high Abbe number $v_e$≥46 ($v_e$=47 for di(TCD methylol) maleate) and even Abbe numbers $v_e$>50 for the other di(TCD methylol) esters specified. Also of significance is good UV transparency of the di(TCD methylol) esters, which is below 10% transmission only at wavelengths below 320 nm for a layer thickness d of 10 mm.

TABLE II

| Substance | Refractive indices at 20° C. $n_e$ (589.3 nm) | Refractive indices at 20° C. $n_e$ (546.1 nm) | Dispersion (Abbe number) $\vartheta e$ DIN 58 884 | Viscosity at 20° C. DIN 51 562 | UV limit-transparency at d = 10 mm T ≤ 10% | Other properties |
|---|---|---|---|---|---|---|
| Di(TCD methylol) phthalate | 1.5497 | 1.5533 | 39 | about 280 000 mPa*s (dynamic) | at 319 nm | |
| Di(TCD methylol) malonate | 1.5166 | 1.5191 | 51 | 1900 mm²/s | at 276 nm and absorption band at 302 nm | Boiling point: 180-185° C. at 10⁻⁵ mbar |
| Di(TCD methylol) succinate | 1.5149 | 1.5173 | 51 | 1600 mm²/s | at 287 nm | |
| Di(TCD methylol) glutarate | 1.5137 | 1.5161 | 51 | 1300 mm²/s | at 286 nm | |
| Di(TCD methylol) adipate | 1.5118 | 1.5142 | 51 | 1100 mm²/s | at 262 nm | Boiling point: 220-225° C. at 10⁻⁵ mbar Pour point: −20° C. (ISO 3016) Flashpoint (COC): 265° C. (ISO 2592) Density $D_{20}$ = 1.090 g/cm³ (DIN 51 757) |
| Di(TCD methylol) sebacate | 1.5057 | 1.5082 | 51 | 800 mm²/s | at 260 nm | |
| Di(TCD methylol) maleate | 1.5258 | 1.5284 | 47 | 9000 mm²/s | at 317 nm | |
| For comparison: TCD alcohol M | 1.5169 | 1.0519 | 52 | 1100 mPa*s (dynamic) 1054 mm²/s (kinematic; calculated) | at 238 nm | Boiling point: 226° C. at 1013 mbar Pour point: −24° C. Flashpoint (COC): 130° C. Density D20 = 1.044 g/cm³ |

Refractive indices and Abbe numbers:

Refractive indices were measured with an Abbe refractometer, from Zeiss, including thermostat, mercury-cadmium spectral lamp and interference filters for 480.0 nm ($n_F$), 546.1 nm ($n_e$)] and 643.8 nm ($n_{C'}$). The dynamic viscosity shown in the table can be converted to the kinematic viscosity by dividing by the density D20.

Calculation of the Abbe number:

$$v_e = \frac{(n_e - 1)}{(n_{p'} - n_{C'})}$$

Kinematic viscosity was determined with an Ubbelohde viscometer according to DIN 51562-1 Jan. 1999 using a Lauda PVS 1 automatic capillary viscometer. The density can be used to interconvert kinematic and dynamic viscosity as is known.

The invention claimed is:

1. An immersion oil for microscopy, comprising:
   a) 15-85% by weight of a first diester A1 based on a tricyclodecane radical K having one functional group and a first hydrocarbon derivative C1 having two functional groups, and
   b) 15-85% by weight of a second diester A2 based on the tricyclodecane radical K having one functional group and a second hydrocarbon derivative C2 having two functional groups,
   wherein C1 and C2 are different
   wherein the tricyclodecane radical K having one functional group is selected from the group consisting of:
   tricyclo[5.2.1.0²,⁶]decane-3-carboxylic acid (TCD carboxylic acid S)

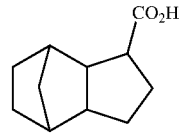 [SMILES: O=C(O)C1CCC2C3CCC(C3)C12]

tricyclo[5.2.1.0²,⁶]decane-4-carboxylic acid (TCD carboxylic acid S)

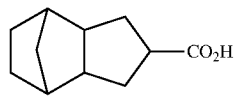 [SMILES: O=C(O)C1CC2C3CCC(C3)C2C1]

tricyclo[5.2.1.0²,⁶]decane-8-carboxylic acid

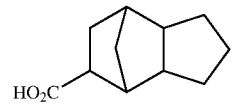

tricyclo[5.2.1.0²,⁶]decane-9-carboxylic acid

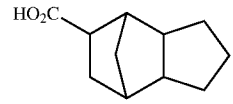

3-hydroxymethyltricyclo[5.2.1.0$^{2,6}$]decane

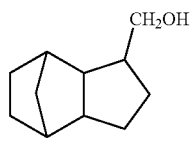 [SMILES: OCC1CCC2C3CCC(C3)C12]

4-hydroxymethyltricyclo[5.2.1.0$^{2,6}$]decane

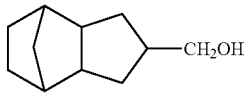 [SMILES: OCC1CC2C3CCC(C3)C2C1]

8-hydroxymethyltricyclo[5.2.1.0$^{2,6}$]decane (TCD alcohol M)

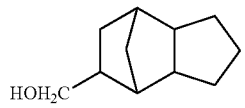

and
9-hydroxymethyltricyclo[5.2.1.0$^{2,6}$]decane

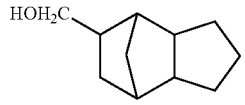 [SMILES: OCC1CC2CC1C1CCCC21]

and said first and second hydrocarbon derivatives C1 and C2 having two functional groups are independently selected from the group consisting of dicarboxylic acids and diols.

2. The immersion oil according to claim 1, wherein the number of carbon atoms in the first hydrocarbon derivative C1 having two functional groups and the number of carbon atoms in the second hydrocarbon derivative C2 having two functional groups differ by at least one carbon atom.

3. The immersion oil according to claim 1, wherein the tricyclodecane radical K having one functional group is selected from the group consisting of:

3-hydroxymethyltricyclo[5.2.1.0$^{2,6}$]decane

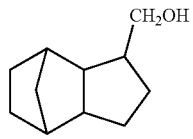 [SMILES: OCC1CCC2C3CCC(C3)C12]

4-hydroxymethyltricyclo[5.2.1.0$^{2,6}$]decane

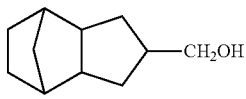

8-hydroxymethyltricyclo[5.2.1.0$^{2,6}$]decane (TCD alcohol M)

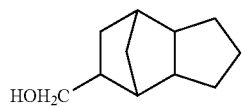

and
9-hydroxymethyltricyclo[5.2.1.0$^{2,6}$]decane

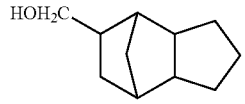 [SMILES: OCC1CC2CC1C1CCCC21]

4. The immersion oil according to claim 1,
wherein the amount of the diesters A1 and A2 satisfies the following conditions:
(i) % by mass(A1)=% by mass(A1)$^E$±5% by mass,
(ii) % by mass(A2)=% by mass(A2)$^E$±5% by mass,
wherein the % by mass(A1)$^E$ and the % by mass(A2)$^E$ correspond to the percentages by mass of A1 and A2 at the eutectic point in a phase diagram of a mixture of A1 and A2.

5. The immersion oil according to claim 1, wherein the dispersion value is within a range from 39±2 to 47±2.

6. The immersion oil according to claim 1, wherein transmission in the visible region is more than 70% at wavelengths greater than 350 nm.

7. The immersion oil according to claim 1, obtainable by:
(a) reacting in a spatially unseparated one-pot reaction
   (i) a tricyclodecane radical K having one functional group and a first hydrocarbon derivative C1 having two functional groups, and
   (ii) the tricyclodecane radical K having one functional group and a second hydrocarbon derivative C2 having two functional groups,
   wherein C1 and C2 are different,
   wherein the reacting produces a reaction product, and
(b) working up, distillative working up, or activated carbon filtering of the reaction product from (a).

8. A method of microscopy, the method comprising:
increasing the numerical aperture of an objective with the immersion oil according to claim 1.

9. A process for producing the immersion oil according to claim 1, the process comprising:
i) providing a first diester A1 and a second diester A2, as a mixture M,
ii) optionally, providing further constituents, and
iii) mixing the first diester A1 and the second diester A2 with any further constituents.

10. The method according to claim 9,
wherein the providing of the mixture M comprises the following:
iv) preparing a solution of a first hydrocarbon derivative C1 having two functional groups and a second hydrocarbon derivative C2 having two functional groups, in a solvent,
v) adding a tricyclodecane radical K having one functional group, thereby producing a reaction mixture, and
vi) optionally, heating the reaction mixture and optionally, adding an esterification catalyst, thereby producing an obtained crude product.

11. The method according to claim 10, wherein vi) is followed by:
vii) removing the obtained crude product, and
viii) optionally, purifying the obtained crude product.

* * * * *

UNITED STATES PATENT AND TRADEMARK OFFICE
CERTIFICATE OF CORRECTION

PATENT NO. : 12,013,523 B2
APPLICATION NO. : 17/213549
DATED : June 18, 2024
INVENTOR(S) : Jaeger et al.

It is certified that error appears in the above-identified patent and that said Letters Patent is hereby corrected as shown below:

In the Specification

Column 1, Line 37, currently reads:
"$(n_c^{23}\ 1.5180(5))$,"
And should read:
--$(n_e^{23}\ 1.5180(5))$,--;

Column 1, Line 41, currently reads:
"mg/i"
And should read:
--mg/l--;

Column 2, Line 19, currently reads:
"23 f 0.1° C.;"
And should read:
--23 ± 0.1° C.;--;

Column 2, Line 20, currently reads:
"1.5180 t 0.0005."
And should read:
--1.5180 ± 0.0005.--;

Column 3, Line 40, currently reads:
"decane-4-carboxylic"
And should read:
--decane-3-carboxylic--;

Column 3, Line 50, currently reads:
"decane-8-carboxylic"

Signed and Sealed this
Fourteenth Day of October, 2025

John A. Squires
*Director of the United States Patent and Trademark Office*

And should read:
--decane-4-carboxylic--;

Column 3, Line 59, currently reads:
"decane-9-carboxylic"
And should read:
--decane-8-carboxylic--;

Column 5, Lines 21-25, currently reads:

" 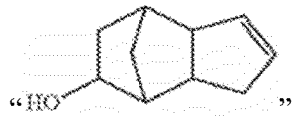 "

Without the "and", and should read:

-- 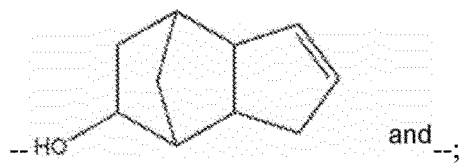 and --;

Column 6, Lines 47-51, currently reads:

" 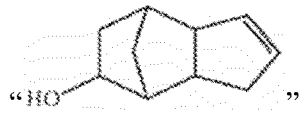 "

Without the "and", and should read:

-- 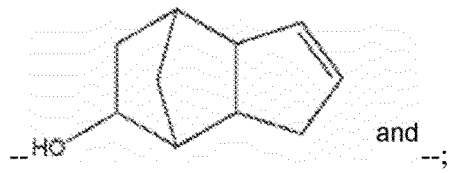 and --;

Column 11, Lines 4-9, currently reads:

" 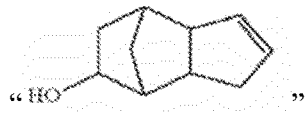 "

Without the "and", and should read:

-- 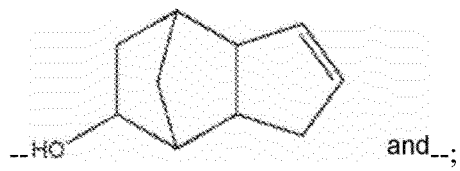 and --;

Column 11, Line 9, currently reads:
"dec-3-ene HO"
And should read:
--dec-3-ene--;

Column 13, Line 54, currently reads:
"$C_1$-$C_{12}$-alkoxyalkylene."
And should read:
--$C_1$-$C_{12}$-alkoxyalkylene,--;

Column 13, Lines 55-56, currently reads:
"$C_4$-alkynylene."
And should read:
--$C_4$-alkynylene,--;

Column 13, Line 59, currently reads:
"$C_7$-$C_{20}$-aralkylene,"
And should read:
--$C_7$-$C_{20}$-arylalkylene,--;

Column 14, Line 10, currently reads:
"$C_1$"
And should read:
--C1--;

Column 14, Line 23, currently reads:
"—C(O)O—."
And should read:
-- —C(O)O—,--;

Column 14, Line 26, currently reads:
"$C_1$-$C_{20}$ haloalkylene."
And should read:
--$C_1$-$C_{20}$-haloalkylene,--;

Column 14, Line 27, currently reads:
"—O—C(O)—."
And should read:
-- —O—C(O)—,--;

Column 14, Line 28, currently reads:
"—C(O)O—."
And should read:
-- —C(O)O—,--;

Column 15, Line 14, currently reads:
"$C_1$-$C_{20}$-haloalkylene."
And should read:
--$C_1$-$C_{20}$-haloalkylene,--;

Column 15, Line 20, currently reads:
"$C_7$-$C_{20}$-aralkylene,"
And should read:
--$C_7$-$C_{20}$-arylalkylene,--;

Column 15, Lines 43-46, currently reads:
""

And should read:
-- 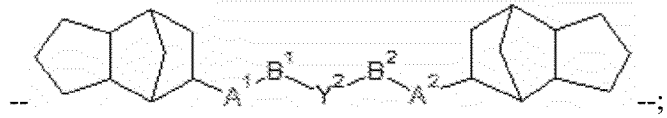 --;

Column 16, Line 31, currently reads:
"$Y^1$"
And should read:
--$Y^2$--;

Column 17, Line 26, currently reads:
"of39-47"
And should read:
--of 39-47--;

Column 18, Lines 63-64, currently reads:
"$C_1$-$C_{12}$-alkoxyalkylene."
And should read:
--$C_1$-$C_{12}$-alkoxyalkylene,--;

Column 19, Line 5, currently reads:
"(lib):"
And should read:
--(IIb):--;

Column 19, Line 18, currently reads:
"—O—C(O)—."
And should read:
-- —O—C(O)—,--;

Column 19, Line 21, currently reads:
"$C_1$-$C_2M$-alkylene,"
And should read:
--$C_1$-$C_{20}$-alkylene,--;

Column 19, Line 26, currently reads:
"$C_1$"

And should read:
--C1--;

Column 19, Line 27, currently reads:
"$C_2$"
And should read:
--C2--;

Column 19, Line 67, currently reads:
"Ca-alkylenearyl."
And should read:
--$C_8$-alkylenearyl,--;

Column 20, Line 19, currently reads:
"C—O—C(O)—."
And should read:
-- —O—C(O)—,--;

Column 20, Line 22, currently reads:
"$C_1$-$C_2$M-alkylene,"
And should read:
--$C_1$-$C_{20}$-alkylene,--;

Column 20, Line 22, currently reads:
"$C_1$-$C_{20}$-haloalkylene."
And should read:
--$C_1$-$C_{20}$-haloalkylene,--;

Column 20, Line 56, currently reads:
"—O—C(O)—."
And should read:
-- —O—C(O)—,--;

Column 20, Line 59, currently reads:
"$C_1$-$C_{20}$-haloalkylene."
And should read:
--$C_1$-$C_{20}$-haloalkylene,--;

Column 21, Lines 20-21, currently reads:
"$C_1$-$C_{12}$-alkoxyalkylene."
And should read:
--$C_1$-$C_{12}$-alkoxyalkylene,--;

Column 21, Line 33, currently reads:
"mixture M."

And should read:
--mixture M,--;
Column 22, Line 13, currently reads:
"Examples 1 to 4"
And should read:
--Examples 1 to 4:--;
Column 22, Line 55, currently reads:
"Table 11"
And should read:
--Table II--;
Column 23, Line 37, currently reads:
"($n_e$)]"
And should read:
--($n_e$)--;
Column 23, Lines 43-45, currently reads:
" 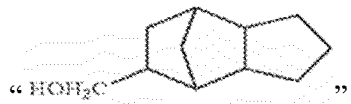 ",
And should read:
-- 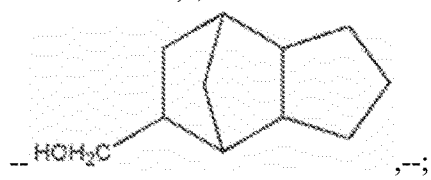 --;
In the Claims
Column 25, Lines 23-26, Claim 1, currently reads:
"  "
With out the ",", and should read:

With out the ".", and should read:
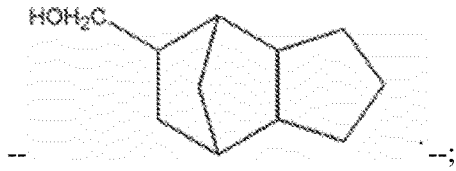
-- --;
Column 26, Line 56, Claim 10, currently reads:
"method"
And should read:
--process--; and
Column 27, Line 1, Claim 11, currently reads:
"method"
And should read:
--process--.